United States Patent [19]

Unoki et al.

[11] Patent Number: 5,629,284
[45] Date of Patent: May 13, 1997

[54] METHOD FOR TREATING RETINAL DISEASES

[75] Inventors: Kazuhiko Unoki; Hitoshi Arimura; Akiko Okubo; Norio Ohba, all of Kagoshima; Takashi Muramatsu; Hisako Muramatsu, both of Nagoya, all of Japan

[73] Assignee: Meiji Milk Products Co., Ltd., Tokyo, Japan

[21] Appl. No.: 505,907

[22] Filed: Jul. 24, 1995

[51] Int. Cl.$^6$ .................. A61K 38/00; A61K 31/725
[52] U.S. Cl. .................................. 514/2; 514/56
[58] Field of Search ............................. 514/2, 56

[56] References Cited

U.S. PATENT DOCUMENTS 3,869,548  3/1975  Dabis ........................ 424/94

OTHER PUBLICATIONS

Medline Abstract 95335377 of Unoki et al., Nippon Ganka Gakkai Zasshi, 99(6), pp. 636–641 Jun. 1995.
Muramatsu, "Midkine: Growth Differentiation Factor Under Control of Retionoic Acid", The Japanese Biochemical Society, Biochemistry, vol. 66, No. 7, 1994.

Unoki et al, "The Relationship Between Retinal Degeneration of White Rats Under Light Irradiation and Midkine Which Is a Retionic Acid–Responsive Growth Factor", 14th Meeting of the Japan Eye–Pharmacological Socieity, Published Aug. 20, 1994.

Unoki et al, "Rescue of Photoreceptors from the Damaging Effects of Constant Light By Midkine, a Retionic Acid––Responsive Gene Product", Investigative Ophthalmology & Visual Science, Nov. 1994, vol. 35, No. 12.

Primary Examiner—Raymond Henley, III
Attorney, Agent, or Firm—Oblon, Spivak, McClelland, Maier & Neustadt, P.C.

[57] ABSTRACT

A method for treating retinal diseases includes administering an effective amount of midkine to patients suffering from retinal diseases. The method of the invention is effective in ameliorating optical disorders of retinas and is quite safe.

3 Claims, 3 Drawing Sheets

METHOD FOR TREATING RETINAL DISEASES

BACKGROUND OF THE INVENTION

1. Field of the Invention

The present invention relates to a method for treating retinal diseases, and more particularly a method for treating diseases caused by light-induced retinal degeneration.

2. Description of the Related Art

Retinal diseases include non-specific retinitis, specific retinitis, proliferating retinitis, retinal periphlebitis, central angiospastic retinitis, exudative retinitis, circinate retinitis, solar retinitis, etc. Aggravation and the onset of these diseases are said to be related to optical disorders of the retina, which disorders are considered to be caused by the generation of superoxides or peroxidation of lipids.

A basic fibroblast growth factor (bFGF) is a member of a family of heparin-binding growth factors. This growth factor exhibits a variety of physiological activities in accelerating the proliferation of fibloblasts, proliferating endothelial cells, and serving as a nerve nutrition factor (Science, Vol. 233, 545-548 (1986). bFGF is also known to suppress retinal disorders of animals caused by light (Proc. Natl. Acad. Sci. U.S.A., Vol., 89, pp 11249-11253 (1992)). Midkine (MK), which was found by Muramatsu et al., is one of a number of factors constituting a new family exhibiting heparin-binding properties. It has also been reported to have a variety of physiological activities which makes it serve as a nerve nutrition factor and a differentiation-inducing factor (Develop. Growth & Differ., 36(1), 1-8 (1994). However, nothing is known as to how MK functions on retinopathies.

Generally speaking, it has been demonstrated that one factor of cytokine exhibits a wide variety of physiological activities, while different factors of it exhibit similar physiological activities. When an attempt is made to apply these cytokine factors to clinical situations, undesirable actions frequently occur in reality instead of intended actions of cytokine. This exemplifies the difficulty in the clinical application of cytokine. Therefore, it is critically important for one who attempts a clinical trial of cytokine to be well aware of details of its biological actions.

Accordingly, a goal of the present invention is to clarify new physiological activities of MK that are not known previously and to pursue the applicability of MK as a medicine.

In view of the foregoing, the present inventors conducted research on the retinal degeneration inhibitory action of MK using animals under conditions of constant light so as to clarify new physiological activities of MK that have formerly been unknown. They tested bFGF in parallel, since bFGF exhibits analogous physiological activities, to clarify the difference in efficacy between MK and bFGF as well as effects that are considered to be an outcome of side reactions. As a result, MK, like bFGF, exhibited an inhibitory action against light-induced retinal degeneration. There was a difference between MK and bFGF in incidence of retinal macrophages, which was considered to be caused by a side reaction. The inventors found that MK was accompanied by a less degree of harmful side effects than bFGF, leading to completion of the invention.

SUMMARY OF THE INVENTION

Accordingly, an object of the present invention is to provide a method for treating retinal diseases.

In one aspect of the present invention, there is provided a method for treating retinal diseases which comprises administering an effective amount of midkine to a patient suffering from a retinal disease.

In another aspect of the present invention, there is provided a method for treating retinal diseases which comprises administering an effective amount of midkine and heparin to a patient suffering from a retinal disease.

In a further aspect of the present invention, there is provided a method for treating retinal diseases which comprises administering an effective amount of midkine and basic fibroblast growth factor to a patient suffering from a retinal disease.

DESCRIPTION OF PREFERRED EMBODIMENTS

Figure 1:
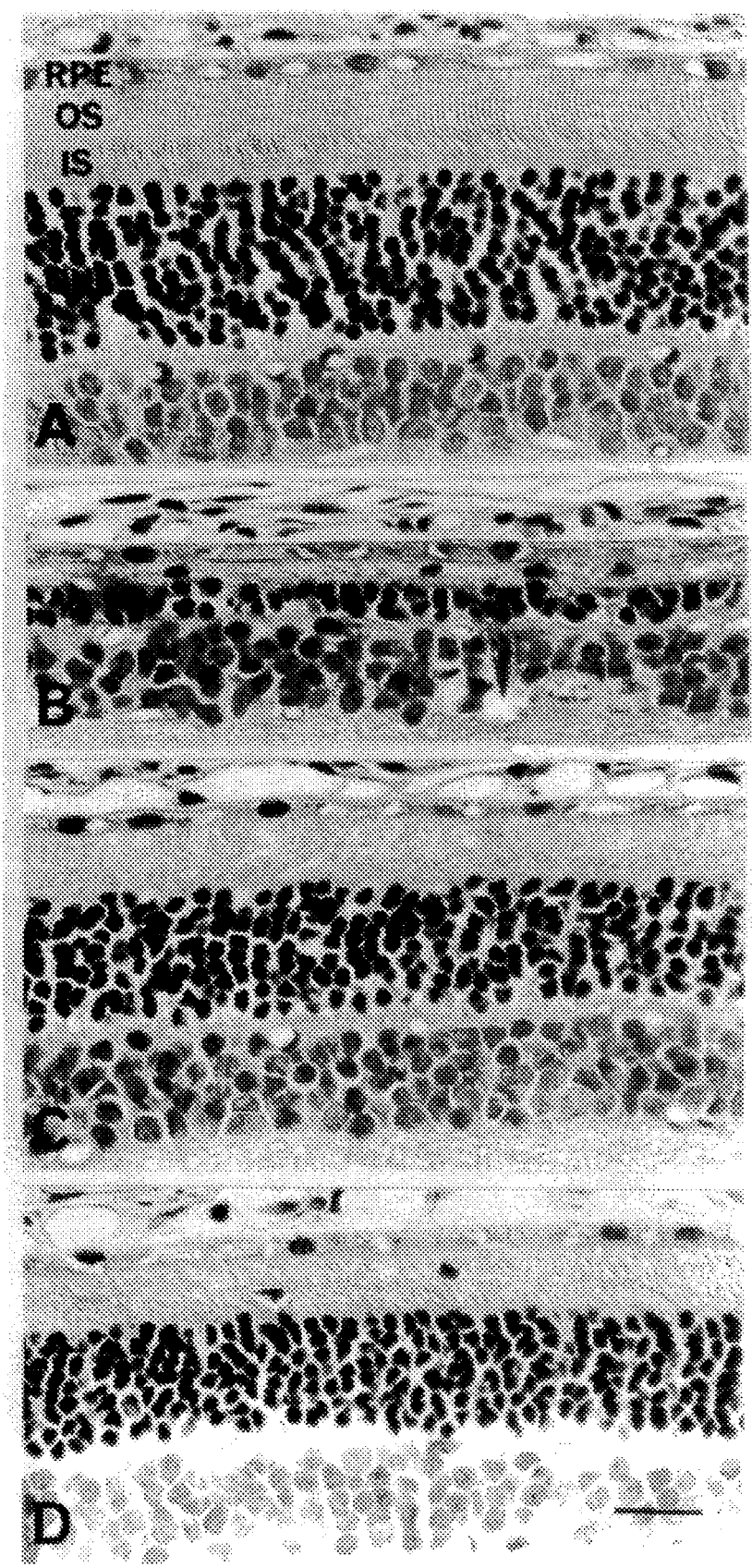
FIG. 1 Light micrographs of the posterior retinas of Sprague-Dawley rats. (A) Normal retina of the rat in cyclic light. The photoreceptor outer and inner segments are distinct, and the outer nuclear layer (ONL) has 9 to 10 rows of photoreceptor nuclei. (B) The retina exposed to constant light for 7 days. The outer and inner segments of photoreceptors are almost lost in this section. The ONL is decreased in thickness, composed of only two to three rows of nucleus, and significantly decreased from the normal ONL. (C) The retina rescued from light damage by an intravitreal injection of MK. The inner segments of photoreceptors are present and almost normal, whereas the outer segments of the photoreceptors are shorter and partially destroyed. The ONL has seven to eight rows of nuclei, although pyknotic nuclei are seen. (D) The retina rescued by bFGF. The outer and inner segments, as well as the ONL, show features similar to those injected with MK. Hematoxylin-eosin. Bar=20 µm. RPE=Retinal pigment epithelium; OS=outer segment of photoreceptor; IS=inner segments of photoreceptor; MK=midkine.

The midkine which is used in the present invention may be prepared by purifying a culture supernatent of recombinant L cells prepared by Tomomura et al. (Biochemical and Biophysical Research Communications, Vol. 171, No. 2, pp. 603-609 (1990)) according to the method of Hisako Muramatsu (Biochemical and Biophysical Research Communications, Vol. 177, No. 2, pp. 652-658 (1991)). Alternatively, it may be prepared by purifying a culture supernatent of recombinant insect cells prepared by Kaneda et al. Regarding the heparin, any heparin that is acceptable for administration to humans is usable. The bFGF may be prepared by extraction from a bovine pituitary gland by a highly purifying method using a heparin affinity chromatography. Alternatively, it may be prepared by a gene recombination technique.

In the present invention, MK may be administered singly or in combination with heparin or bFGF. When MK is combined with heparin or bFGF, the therapeutic effect in the treatment of retinitis is even more enhanced.

The amount of MK to be administered to humans is not particularly limited as long as it is an effective amount. Generally, an amount of 3 to 60 µg/kg is preferable. When MK is used along with heparin, it is preferred that the amount of MK be from 3 to 60 µg/kg and that of heparin be from 55 to 165 µg/kg. Moreover, when MK is used along with bFGF, the amount of MK is preferably from 3 to 60 µg/kg and that of bFGF is preferably from 3 to 60 µg/kg.

The effective components of the present invention are administered by way of eye drops or injections, of which injections are more preferable. When MK is used in the form of an eye drop or an injection, it is preferably used as a composition along with pharmaceutically acceptable carriers. Examples of pharmaceutically acceptable carriers include water, saline, and various buffers. Stabilizers, solubilizers and similar materials may also be incorporated in the composition.

As described in the following example, MK possesses excellent activities in ameliorating light-induced damage of retinas. In addition, since MK does not allow macrophages to migrate, patients' pains are suppressed and better prognosis is expected. Thus, the method of the invention is safe and useful in the treatment of a variety of retinal diseases. More specifically, the method of the present invention is useful for the following diseases and conditions among others.

(1) Retinal degenerations and dystrophies:
    retinitis pigmentosa, cone dystrophy, and heredity vitreoretinal degenerations.
(2) Macula degenerations:
    age-related macular degenerations, and macula dystrophies.
(3) Macula hole.
(4) Diabetic retinopathy.
(5) Retinal vascular diseases:
    central retinal vein occulusion, retinal branch vein occulusion, retinal arterial obstructive diseases, retinopathy of prematurity, and the ocular ischemic diseases.
(6) Inflammatory diseases:
    ocular toxoplasmosis, cytomegalovirus infections of retina, acute retinal necrosis syndrome, fungal infection of the retina, and Vogt-Koyanagi-Harada syndrome.
(7) Photic retinal injury.
(8) Trauma of the retina.
(9) Retinal detachment.
(10) Proliferative vitreoretinopathy.
(11) Retinoblastoma.
(12) Melanoma of uvea.
(13) Glaucoma.
(14) Corneal endotheliopathy.
(15) Corneal epitheliopathy.

EXAMPLES

The present invention will next be described by way of an example, which should not be construed as limiting the invention.

(1) Materials and Methods

Animals

Sprague-Dawley albino rats were obtained at 2 to 3 months of age (Kyudo, Kumamoto, Japan) and maintained in a 12-hour light/12-hour dark cycle (with an in-cage illuminance of less than 15 foot-candles) for at least 7 days before use. All procedures followed the ARVO Statement for the Use of Animals in Ophthalmic and Vision Research and the guidelines of the Kagoshima University Faculty of Medicine for Animal Research.

Factors

Midkine, MK plus heparin, bFGF, and heparin were injected into the vitreous cavity of a rat. Midkine was purified from the culture medium of L-cells transfected with an MK expression vector, and was concentrated to 1 µg/µl. Human recombinant bFGF (1 µg/µl; R & D Systems, Minneapolis, Minn.) and heparin (8.2 units/µl; Nakarai Tesque, Kyoto, Japan) were commercially available. The control vehicle was phosphate-buffered saline (PBS).

Injection and Histologic Procedures

Two days before constant light exposure, rats were anesthetized with an intramuscular injection of ketamine (84 mg/kg)—xylazine (6 mg/kg) mixture. A single 1 µl of solution containing various agents was then injected into the vitreous of one eye.

The other eye of each rat was injected with the same volume of PBS as a control. The injections were performed with a 32-gauge beveled needle injected through the sclera, choroid and retina at a point midway between the ora serrata and the equator of the eye. Two days later, the rats were placed into constant light at an illuminance of 130 fc to 150 fc (1 fc=10.76 lux) for 1 week. After the constant light exposure, the rats were killed by an overdose of carbon dioxide and perfused intravascularly with a phosphate-buffered mixture of 2% paraformaldehyde and 2.5% glutaraldehyde. The eyes were enucleated, bisected along the vertical meridian, and rinsed in PBS, dehydrated in a graded series of ethanol, and embedded in paraffin. The eyes were sectioned at 3 µm thickness and stained with hematoxylin—eosin. Each section cut along the vertical meridian of the eye contained the entire retina, extending from the ora serrata in the superior hemisphere to the ora serrata in the inferior hemisphere and passing through the optic nerve head. Sections prepared in this manner seldom contained oblique regions.

Quantification of Constant Light Damage and Rescue Effect

The thickness of the outer nuclear layer (ONL) was measured as an index of photoreceptor loss to quantify the light-induced retinal degeneration. A mean ONL thickness was obtained from a single section of each eye. In each of the superior and inferior hemispheres, four sets of color slides were taken; each set was centered 700 µm from the retina (the diameter of the microscope field was ×200 magnification). The first set of measurements was taken approximately 175 µm from the optic nerve head, and subsequent sets were located more peripherally. Each color slide was transferred to a computer using a Nikon Coolscan (Nikon, Tokyo, Japan) and the ONL thickness was determined by four sets of six measurements each using an NIH Image on the computer screen. Within each 700 µm of retina, the six measurements were made at defined points 100 µm apart using a scale on the screen. In this way, 48 measurements in two hemispheres sampled representative regions of almost the entire section.

The rescue effects of each agent were analyzed assigning a relative score to the control eye described. This method considered not only ONL thickness but also the integrity and organization of the inner and outer segments, as well as the distribution and extent of rescue and degeneration within each eye. For assessing the overall degree of photoreceptor rescue, each section was compared with its contralateral control eye, and the degree of rescue was given a value from 0+ to 4+. Zero indicated no rescue and 4+ was maximal, with at least some regions of the retina appearing almost normal.

For macrophage counts, the number of cells was counted in the photoreceptor, inner plexiform, and ganglion cell layer, which had the appearance of a macrophage in a single section from each rat eye. Cells that were obviously neurons, glia, or those associated with blood vessels were omitted.

For each of the experiments, the number of eyes measured is given in parentheses at the bottom of the figures. The measurements of ONL thickness and macrophage counts of treated eyes were compared with those of control eyes, using Student's t-test.

Results

Degeneration of photoreceptor cells after 1 week of constant light in uninjected rats and those injected with PBS was most severe in the posterior to equatorial region of the superior hemisphere. The ONL was reduced in thickness from the normal nine to ten rows of photoreceptor nuclei (FIG. 1A) to one to three rows (FIG. 1B). Only a few fragments of photoreceptor inner and outer segments were saved in this most damaged region. The retinal pigment epithelium (RPE) did not show any damage. In other parts of the light-damaged retina, the inner and outer segments of photoreceptors were damaged to a lesser degree, and the ONL was thicker. The peripheral region of the inferior hemisphere had the least damage from the constant light exposure.

Intravitreal injection with MK, MK plus heparin, and bFGF significantly rescued the photoreceptors and ONL (FIGS. 1C, 1D). The photoreceptors had inner and outer segments and sometimes appeared even normal, although they were a little shortened and disorganized. The ONL had seven to eight rows of nuclei, although pyknotic nuclei were scattered throughout the layer.

Figure 2:
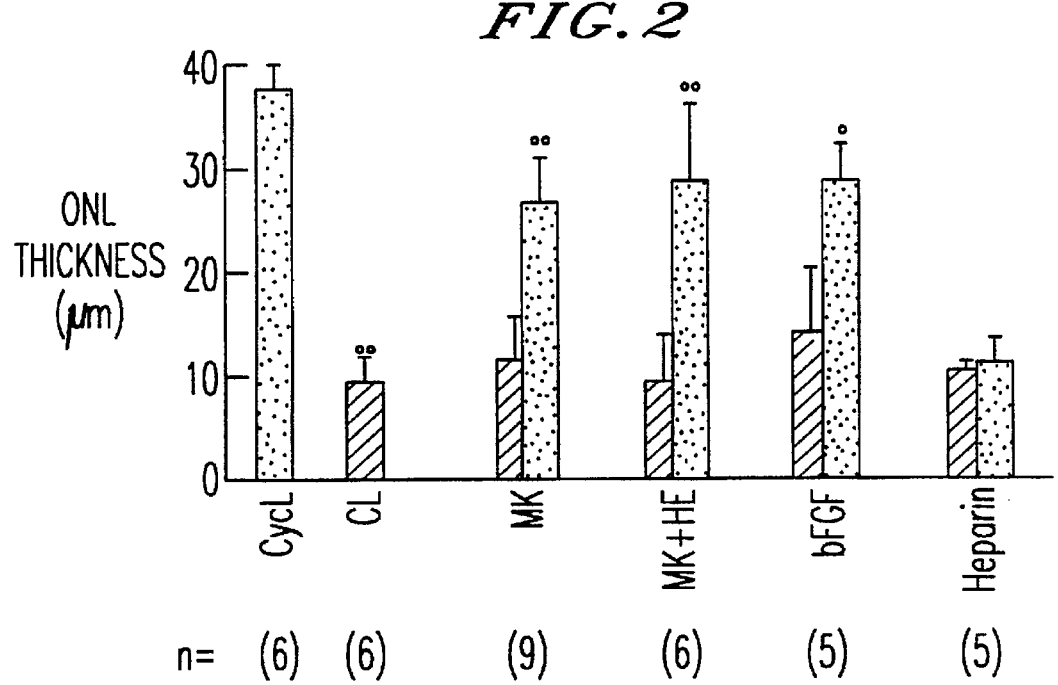
FIG. 2 Measurements (mean ± standard deviation) of the ONL thickness in eyes exposed to cyclic light (Cyc L), exposed to constant light for 7 days without any injection (CL), and with various agents injected 2 days before light exposure. The agents are midkine (MK), MK plus heparin (MK +Hep), bFGF, and heparin. Controls for each agent (PBS) injected 2 days before light exposure. The number of rats injected (with an equal number of control eyes) was nine for MK, six for MK plus heparin, five for bFGF, and five for heparin. Bar=mean value; error bar=standard deviation. Outer nuclear layer thickness of eyes injected with MK, MK plus heparin, and bFGF shows significant differences in numbers of photoreceptor nuclei surviving (shaded bars) when compared with control eye (solid black bars). *P<0.001, **P<0.0001. Heparin does not show any significant difference from the control.

The thickness of the ONL in the uninjected and PBS-injected eyes was approximately 25% of that seen in normal cyclic light (FIG. 2). The thickness of the eye injected with MK showed a considerable rescue in constant light-damaged retina (approximately 75% of the normal thickness; P <0.0001). The rescue activity of bFGF was similar to that of MK and also to that previously demonstrated (LaVail MM etal, Proc. Natl. Acad. Sci. USA, 89, 11249–11253 (1992); Faktovich EG, J. Neurosci., 12, 3554–3567 (1992). The combination of MK and heparin revealed a slightly greater degree of rescue than did MK alone, as did bFGF; however, the difference between the degree of rescue for bFGF and that of MK alone was not statistically significant. The injection of heparin alone did not show any rescue effects compared with that of PBS.

Figure 3:
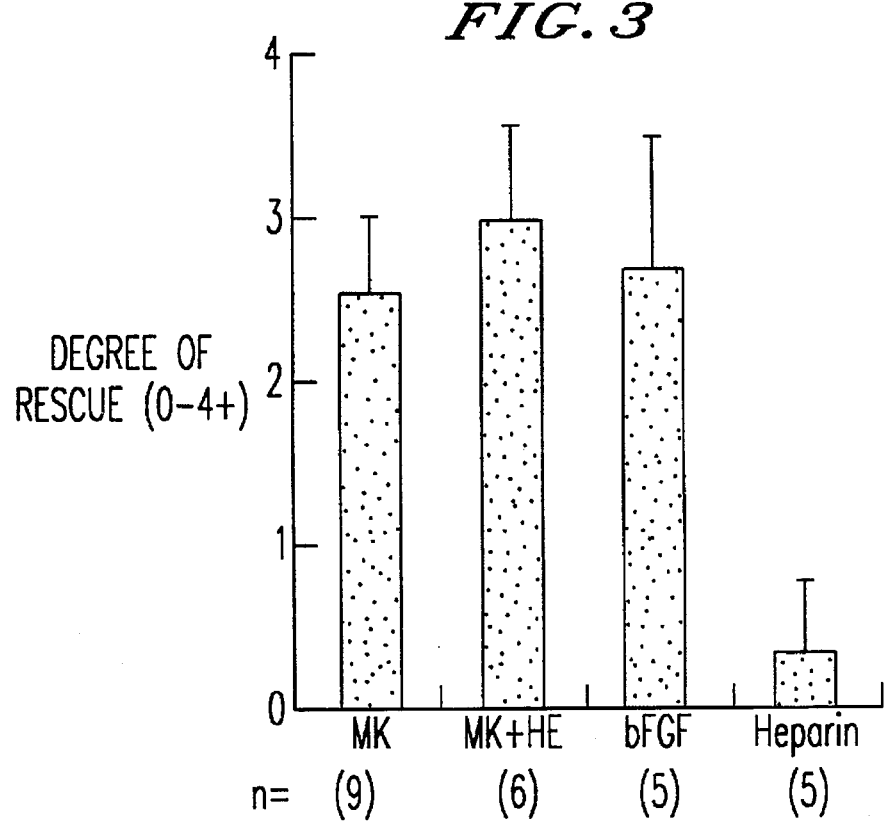
FIG. 3 The scores for the degree of photoreceptor rescue (mean ± standard deviation) by various agents. The scores of photoreceptors rescued by various agents were similar to those obtained by measuring the outer nuclear layer thickness. The rats scored were the same as those used in the experiments described in FIG. 2. The abbreviations are also the same as those described in the legend to FIG. 2.

FIG. 3 shows the rescue effect of various agents as determined by the scoring system described in the Methods section. The eye that received the factor was given a score relative to that injected with PBS, as previously reported. The overall results were similar to those of the ONL thickness. Midkine and bFGF revealed similar survival effects on constant light-induced retinal degeneration, and MK plus heparin had the highest score (FIG. 3). The eyes injected with heparin had a low score.

Figure 4:
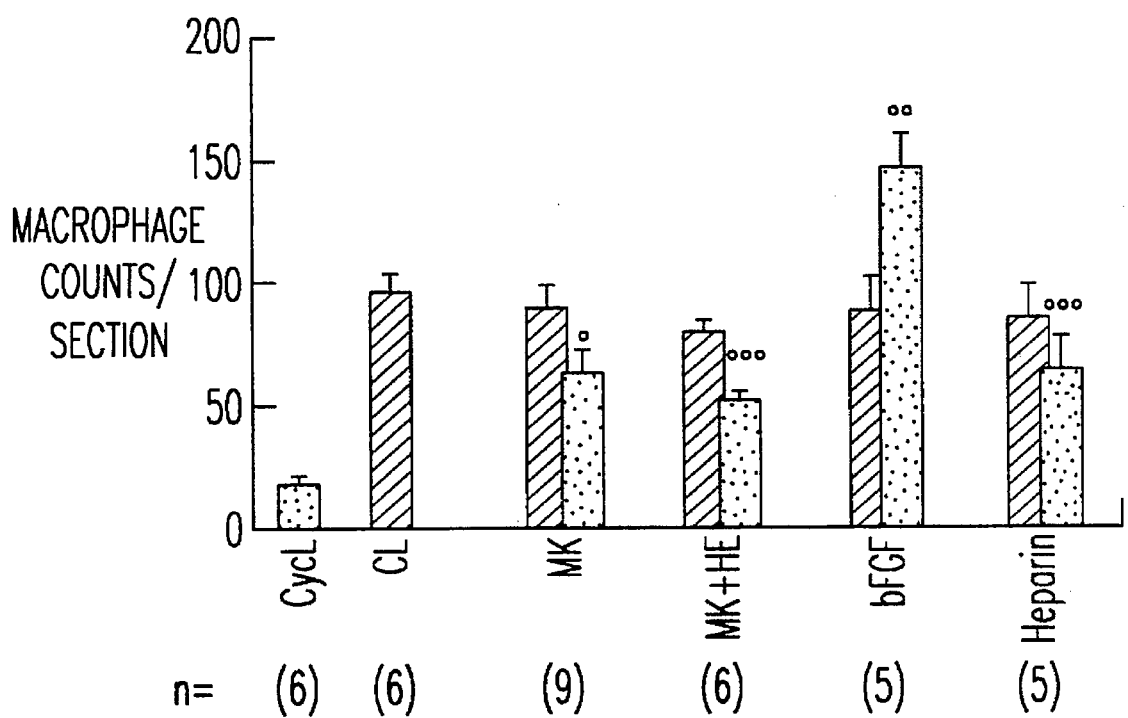
FIG. 4 The counts of macrophages (mean ± standard deviation) in various retinas. Macrophages were counted in the same rats used in FIG. 2. The counts of macrophages in the constant light-damaged retina with or without injection of PBS increased significantly compared with those in normal retinas (solid black bars). #P<0.0001. MK reduced the macrophage incidence (P<0.01). MK plus heparin and heparin only suppressed the number of macrophages to 30% of the uninjected and PBS-injected constant light-damaged retina (P<0.0001). bFGF intravitreal injection significantly increased the number of macrophages compared with uninjected eyes and those injected with PBS (P<0.001). *P<0.01; P<0.001; *<0.0001.

Injection of bFGF into the RCS (Royal College of Surgeons) rat with inherited retinal dystrophy and the albino Sprague-Dawley rat with light-induced retinal degeneration increased the number of retinal macrophages. The number of macrophages in the photoreceptor as well as in the inner plexiform and ganglion cell layers was counted. The eyes injected with bFGF had 1.5 times the number of macrophages in PBS-injected eyes (FIG. 4). However, the number of macrophages in eyes injected with MK was reduced to 70% of the number in eyes injected with PBS. The addition of heparin to MK suppressed the value to 60%.

These results indicate that MK, the product of a retinoic responsive gene, promotes the survival of eyes subjected to constant light-induced retinal degeneration in the albino Sprague-Dawley rat. The degree of rescue from light damage by MK was almost the same as that by bFGF.

The injection of bFGF into the vitreous of rats with either inherited or light-induced retinal degeneration increases the incidence of retinal macrophages; this is one of several potentially harmful side effects. It is of interest that the injection of MK into the vitreous reduced the number of macrophages from that usually seen in light damage. The rescue by MK is independent of macrophage involvement. Retinoic acid prevents the outgrowth of RPE cells in vitro and shows antiproliferative effects on proliferative vitreoretinopathy in an animal model. Because MK is the product of a retinoic acid-responsive gene, the injection of MK may be effective and harmless for the treatment of human retinal diseases.

What is claimed is:

1. A method of treating a retinal disease comprising administering an effective amount of midkine to a patient suffering from a retinal disease.

2. A method of treating a retinal disease comprising administering an effective amount of midkine and heparin to a patient suffering from a retinal disease.

3. A method of treating a retinal disease comprising administering an effective amount of midkine and basic fibroblast growth factor to a patient suffering from a retinal disease.

* * * * *